US012264220B2

(12) United States Patent
Lobert et al.

(10) Patent No.: US 12,264,220 B2
(45) Date of Patent: Apr. 1, 2025

(54) PROCESS FOR PRODUCING HIGH-PURITY HYDROSILYLATION PRODUCTS

(71) Applicant: Evonik Operations GmbH, Essen (DE)

(72) Inventors: Matthias Lobert, Essen (DE); Thomas Reibold, Herten (DE)

(73) Assignee: Evonik Operations GmbH, Essen (DE)

( * ) Notice: Subject to any disclaimer, the term of this patent is extended or adjusted under 35 U.S.C. 154(b) by 641 days.

(21) Appl. No.: 17/142,947

(22) Filed: Jan. 6, 2021

(65) Prior Publication Data
US 2021/0238361 A1 Aug. 5, 2021

(30) Foreign Application Priority Data
Jan. 30, 2020 (EP) .................. 20154483

(51) Int. Cl.
A01N 25/10 (2006.01)
A61K 8/891 (2006.01)
C08G 77/08 (2006.01)
C08G 77/18 (2006.01)
D06M 15/643 (2006.01)

(52) U.S. Cl.
CPC ............ C08G 77/18 (2013.01); A01N 25/10 (2013.01); A61K 8/891 (2013.01); C08G 77/08 (2013.01); D06M 15/643 (2013.01)

(58) Field of Classification Search
CPC ......... C08G 77/18; A01N 25/10; A61K 8/891
See application file for complete search history.

(56) References Cited

U.S. PATENT DOCUMENTS

| 2,823,218 | A | | 2/1958 | Speier et al. |
| 3,278,457 | A | | 10/1966 | Milgrom |
| 3,278,458 | A | | 10/1966 | Belner |
| 3,278,459 | A | | 10/1966 | Johnston |
| 3,427,256 | A | | 2/1969 | Milgrom |
| 3,427,334 | A | | 2/1969 | Belner |
| 3,427,335 | A | | 2/1969 | Herold |
| 3,775,452 | A | | 11/1973 | Karstedt |
| 4,044,038 | A | | 8/1977 | Rossmy |
| 5,021,512 | A | * | 6/1991 | Woods .................. C08G 77/38 525/328.2 |
| 5,247,045 | A | | 9/1993 | Durfee et al. |
| 5,391,679 | A | | 2/1995 | Burkhart et al. |
| 5,470,813 | A | | 11/1995 | Le-Khac |
| 5,482,908 | A | | 1/1996 | Le-Khac |
| 5,696,192 | A | * | 12/1997 | Harashima .............. C08K 3/32 524/415 |
| 6,194,596 | B1 | | 2/2001 | Josten et al. |
| 6,255,511 | B1 | | 7/2001 | Klein et al. |
| 6,291,622 | B1 | | 9/2001 | Droese et al. |
| 6,437,162 | B1 | * | 8/2002 | O'Lenick, Jr. .......... C08G 77/46 556/445 |
| 6,489,498 | B2 | | 12/2002 | Klein et al. |
| 7,196,153 | B2 | | 3/2007 | Burkhart et al. |
| 7,612,158 | B2 | | 11/2009 | Burkhart et al. |
| 7,619,035 | B2 | * | 11/2009 | Henning ................ C08G 77/06 528/25 |
| 7,635,581 | B2 | | 12/2009 | Ferenz et al. |
| 7,829,647 | B2 | | 11/2010 | Bruckner et al. |
| 8,022,150 | B2 | | 9/2011 | Esselborn et al. |
| 8,076,440 | B2 | | 12/2011 | Kuppert et al. |
| 8,138,294 | B2 | | 3/2012 | Henning et al. |
| 8,198,473 | B2 | | 6/2012 | Ferenz et al. |
| 8,283,422 | B2 | | 10/2012 | Schubert et al. |
| 8,334,355 | B2 | | 12/2012 | Henning et al. |
| 8,420,748 | B2 | | 4/2013 | Henning et al. |
| 8,470,306 | B2 | | 6/2013 | Neumann et al. |
| 8,497,338 | B2 | | 7/2013 | Bai et al. |
| 8,557,944 | B2 | | 10/2013 | Henning et al. |
| 8,598,295 | B2 | | 12/2013 | Henning et al. |
| 8,778,319 | B2 | | 7/2014 | Herrwerth et al. |
| 8,796,198 | B2 | | 8/2014 | Henning et al. |
| 8,883,932 | B2 | | 11/2014 | Brugger et al. |
| 8,916,511 | B2 | | 12/2014 | Maurer et al. |
| 8,946,369 | B2 | | 2/2015 | Henning et al. |
| 9,035,011 | B2 | | 5/2015 | Ferez et al. |
| 9,051,424 | B2 | | 6/2015 | Lobert et al. |
| 9,334,354 | B2 | | 5/2016 | Ferenz et al. |
| 9,346,919 | B2 | | 5/2016 | Jakewitsch et al. |
| 9,434,749 | B2 | * | 9/2016 | Roy .......................... C07F 7/14 |
| 9,550,928 | B2 | | 1/2017 | Lobert et al. |

(Continued)

FOREIGN PATENT DOCUMENTS

CN 103987759 A 8/2014
CN 104788679 7/2015

(Continued)

OTHER PUBLICATIONS

Bouvet-Marchand et al. (Influence of experimental parameters on the side reactions of hydrosilylation of allyl polyethers studied by a fractional factorial design, Reaction Chemistry & Engineering, 2018). (Year: 2018).*
Dupont Data Sheet (Year: 2019).*
Shin et al. (Careful Investigation of the Hydrosilylation of Olefins at Poly(Ethylene Glycol) Chain Ends and Development of a New Silyl Hydride to Avoid Side Reactions, Journal of Polymer Science, 2017) (Year: 2017).*
Matthey, Platinum Catalysts for Hydrosilylation, 2010 (Year: 2010).*
Rashid et al., Magnesium Silicate, 2011 (Year: 2011).*
European Search Report mailed on Jul. 27, 2020 in EP 20154483.0 (21 pages).
Maciejewski H. et al., "Silicone waxes-synthesis via hydrosilylation in homo-and heterogeneous systems," Journaly of Molecular Catalysis A: Chemical, Elsevier, Amsterdam, NL, Bd. 257, Nr. 1-2, Copyright Sep. 2006, pp. 141-148 (8 pages).

(Continued)

Primary Examiner — Andrew S Rosenthal
Assistant Examiner — Danielle Kim
(74) Attorney, Agent, or Firm — Grüneberg and Myers PLLC

(57) ABSTRACT

The present invention relates to a process for producing high-purity hydrosilylation products, and also to the products that may be produced by this process and to the use thereof as surfactants.

19 Claims, No Drawings

(56) References Cited

U.S. PATENT DOCUMENTS

| | | | |
|---|---|---|---|
| 9,657,144 | B2 | 5/2017 | Hubel et al. |
| 9,896,534 | B2 | 2/2018 | Lobert et al. |
| 9,993,786 | B2 | 6/2018 | Roland et al. |
| 10,087,278 | B2 | 10/2018 | Lobert et al. |
| 10,160,832 | B2 | 12/2018 | Lobert et al. |
| 10,301,427 | B2 | 5/2019 | Lobert et al. |
| 10,407,546 | B2 | 9/2019 | Lobert et al. |
| 10,544,267 | B2 | 1/2020 | Knott et al. |
| 10,894,801 | B2 | 1/2021 | Albert et al. |
| 2004/0014925 | A1 | 1/2004 | Hell et al. |
| 2004/0087471 | A1* | 5/2004 | Osinga ............. C11D 7/14 510/511 |
| 2006/0016729 | A1* | 7/2006 | Guennouni |
| 2006/0167296 | A1* | 7/2006 | Guennouni ............. C07F 7/20 556/466 |
| 2007/0128143 | A1 | 6/2007 | Gruning et al. |
| 2010/0248325 | A1 | 9/2010 | Eckstein et al. |
| 2012/0028022 | A1 | 2/2012 | Brugger et al. |
| 2013/0035407 | A1 | 2/2013 | Lobert et al. |
| 2013/0259821 | A1 | 10/2013 | Henning et al. |
| 2013/0331592 | A1 | 12/2013 | Hartung et al. |
| 2015/0004112 | A1 | 1/2015 | Ritter et al. |
| 2015/0004113 | A1 | 1/2015 | Ritter et al. |
| 2017/0145258 | A1* | 5/2017 | Swier ............. C04B 26/32 |
| 2017/0240692 | A1 | 8/2017 | Roland et al. |
| 2018/0016392 | A1 | 1/2018 | Lobert et al. |
| 2020/0377640 | A1 | 12/2020 | Knott et al. |
| 2020/0377663 | A1 | 12/2020 | Favresse et al. |
| 2020/0377668 | A1 | 12/2020 | Favresse et al. |
| 2021/0047474 | A1 | 2/2021 | Klostermann et al. |
| 2021/0206972 | A1 | 7/2021 | Schulz et al. |
| 2021/0229066 | A1* | 7/2021 | Malaba ............. B01J 20/24 |
| 2022/0315709 | A1 | 10/2022 | Reibold et al. |

FOREIGN PATENT DOCUMENTS

| | | | |
|---|---|---|---|
| CN | 105176409 | 12/2015 | |
| DE | 693 10 619 T2 | 12/1997 | |
| DE | 10 2004 018 926 A1 | 11/2005 | |
| DE | 10 2005 004 676 A1 | 8/2006 | |
| DE | 10 2007 055 485 A1 | 6/2009 | |
| DE | 10 2008 041 601 A1 | 3/2010 | |
| DE | 10 2011 005 607 A1 | 9/2012 | |
| EP | 0 887 367 A2 | 12/1998 | |
| EP | 1 439 200 A1 | 7/2004 | |
| EP | 3 663 371 | 6/2020 | |
| EP | 4067411 A1 | 10/2022 | |
| JP | 2003 082103 | 3/2003 | |
| WO | WO-2008043512 A2 * | 4/2008 | ............. A61K 8/062 |
| WO | 2012/130674 A2 | 10/2012 | |
| WO | 2013/017365 A1 | 2/2013 | |
| WO | 2013/066983 A1 | 5/2013 | |
| WO | 2017/213809 A1 | 12/2017 | |
| WO | 2018/001889 A1 | 1/2018 | |

OTHER PUBLICATIONS

Bai, "In Situ Platinum Recovery and Color Removal from Organosilicon Streams," Industrial & Engineering Chemistry Research, copyright 2012, 51, pp. 16457-16466 (10 pages).

Dr. Walter Noll, "Chemie und Technologie der Silicone" [Chemistry and Technology of Silicones], Verlag Chemie, Kap 2, 1960, pp. 20-51, with partial English translation.

Marion et al., U.S. Appl. No. 18/715,791, filed Jun. 3, 2024.

U.S. Appl. No. 18/715,791, filed Jun. 3, 2024, Marion et al.

Database WPI, Week 200377, 2017, 2 pages, XP002799656, Reference JP2003-082103 previously filed, submitting English abstract only.

Office Action received for European Patent Application No. 21152712.2, mailed on Oct. 11, 2024, 5 pages.

* cited by examiner

PROCESS FOR PRODUCING HIGH-PURITY HYDROSILYLATION PRODUCTS

CROSS REFERENCE TO RELATED APPLICATIONS

This application is a 35 U.S.C. § 119 patent application which claims the benefit of European Application No. 20154483.0 filed Jan. 30, 2020, which is incorporated herein by reference in its entirety.

FIELD

The present invention is in the field of silicones. It relates in particular to a process for producing high-purity hydrosilylation products, and also to the products that may be produced by this process and to the use thereof, particularly as surfactants.

Hydrosilylation products are understood by a person skilled in the art to be preferably SiC-bonded organomodified siloxanes, especially polyether siloxanes, which with its widely adjustable surfactant characteristics represent an industrially very important substance class.

Hydrosilylation reactions of siloxanes bearing SiH groups and/or silanes with compounds comprising a C=C double bond are carried out continuously or discontinuously and in each case in the presence of a noble metal catalyst.

Appropriate catalytically active compounds of platinum, palladium, rhodium, ruthenium, iridium and osmium are known to those skilled in the art.

In the prior art, usually employed is the platinum metal-catalyzed addition of siloxanes bearing SiH groups and silanes to olefinically functionalized compounds, such as to allyl polyethers, as described for example in the book "Chemie und Technologie der Silicone" [Chemistry and Technology of Silicones], Verlag Chemie, 1960, page 43, and in the patent literature.

The catalysts which have become established in current operational practice are predominantly Pt catalysts such as hexachloroplatinic acid (U.S. Pat. No. 2,823,218), cis-diamminedichloridoplatinum(II) and Karstedt's catalyst (U.S. Pat. No. 3,775,452).

The platinum catalysts are mostly present in the reaction mixture as homogeneous catalysts and may often remain in the final product. However, due to increasing market requirements, there also exists an ever-growing demand for Pt-free products. In addition to ecological aspects, such as the recovery of important noble metal resources, also increasingly in focus is the improvement of intrinsic product quality.

Hydrosilylation products having elevated noble metal content in general and elevated Pt content in particular usually exhibit the problem of darker color of the product directly after production, however sometimes the color also changes over time, both however representing a distinct quality defect. A further quality defect is also the slow formation of black particles, frequently occurring with ageing, due to precipitating noble metal.

BACKGROUND

These facts frequently result in customer complaints and this quality defect consequently should be remedied.

Diverse solution approaches are known in the prior art, such as is apparent from the scientific article *Ind. Eng. Chem. Res* 2012, 51, 16457-16466 and the literature cited therein.

In addition to membrane technology, solvent extraction and selective precipitation, the use of adsorbents is broadly established.

Suitable adsorbents are, for example, acidic or basic ion exchangers, chelating agents or functionalized silica gels (WO 2017213809 A1), activated carbon (CN 20150692397) or carbon black (CN201510199280).

However, the use of such adsorbents requires a further time-consuming process step of 4 hours after the actual hydrosilylation reaction, as described, for example, in WO 2017213809 A1.

An efficient removal of noble metal can be achieved by the use of supported catalysts. Isolation of the catalyst is easily possible by simple filtration but the disadvantage here is that the supported catalyst has to be specially prepared.

U.S. Pat. No. 8,497,338 B2 describes a process based on this concept, where the hydrosilylation process is carried out in such a way that the reaction medium is fed through a catalyst fixed bed.

SUMMARY

In addition to the problem that such a fixed bed can bleed and after a certain service life has to be exchanged with considerable technical and personnel effort, substantial investments are also required to build new plants which enable a hydrosilylation reaction on a fixed bed in continuous mode.

Since hydrosilylation reactions are predominantly carried out in batchwise or semi-batchwise mode, there is a need to facilitate a simple and particularly inexpensive process for producing hydrosilylation products, in which especially the provision of particularly high-purity hydrosilylation products is facilitated.

DETAILED DESCRIPTION

In the context of the present invention, it has been found, surprisingly, that carrying out a noble metal-catalyzed hydrosilylation of a H-functional siloxane with an unsaturated organic compound in the presence of adsorbents, which are added as a further, separate component, results in color-reduced and preferably colorless, and thus particularly high-purity, hydrosilylation products. However, the color reduction arises without use of separately added adsorbents compared to an otherwise analogous procedure.

In the context of the present invention, it has also been found, surprisingly, that carrying out a noble metal-catalyzed hydrosilylation of a H-functional siloxane with an unsaturated organic compound in the presence of adsorbents, which are added as a further, separate component, and water results in qualitatively even better, and even higher-purity, hydrosilylation products.

The present invention accordingly relates to a process for producing organically modified polysiloxanes and/or silanes by hydrosilylation, comprising the following steps:
a) reacting a SiH-functional siloxane and/or silane with an unsaturated organic compound in the presence of a noble metal catalyst and
   optionally in the presence of water,
b) optional distillation,
c) final separation of solids, especially by filtration,
in which adsorbents are used in step a) and are added as a further, separate component.

Accordingly, in the process according to the invention, at least 4 different components are added: (i) SiH-functional siloxane and/or silane; (ii) unsaturated organic compound;

(iii) noble metal catalyst; (iv) adsorbents. The components (iii) and (iv) to be added are different components.

The present invention also relates to hydrosilylation products, produced by the process according to the invention, and also to the use thereof, for example as surfactants.

The terms "polysiloxane" and "siloxane" are used synonymously in the context of the present invention.

The subject matter of the invention will be described by way of example below, without any intention that the invention be restricted to these illustrative embodiments. Where ranges, general formulae or classes of compounds are specified below, these are intended to encompass not only the corresponding ranges or groups of compounds which are explicitly mentioned but also all subranges and subgroups of compounds which can be obtained by removing individual values (ranges) or compounds. Where documents are cited in the context of the present description, the entire content thereof, particularly with regard to the subject matter that forms the context in which the document has been cited, is intended to form part of the disclosure content of the present invention. Where chemical (empirical) formulae are used in the present invention, the specified indices can be not only absolute numbers but also average values. For polymeric compounds, the indices preferably represent average values. Unless stated otherwise, percentages are figures in percent by weight. If measured values are reported hereinbelow, these measurements, unless stated otherwise, have been conducted under standard conditions (20° C. and 1013 mbar). When average values are reported below, the values in question are weight averages, unless stated otherwise.

The word fragment "poly" encompasses in the context of this invention not just compounds having at least 3 repeating units of one or more monomers in the molecule, but in particular also compositions of compounds having a molecular weight distribution and having an average molecular weight of at least 200 g/mol. This definition takes account of the fact that it is customary in the field of industry in question to refer to such compounds as polymers even if they do not appear to conform to a polymer definition as per OECD or REACH guidelines.

In the process according to the invention, SiH-functional siloxanes are used. These are known as such to those skilled in the art. The provision of the SiH-functional siloxanes for the process according to the invention is preferably effected by performing the known prior art process of equilibration, preferably over a sulfonated resin. The equilibration of branched or linear, optionally hydrosilylated poly(organo) siloxanes having end and/or pendant SiH functions is described in detail in the prior art, for example in the documents EP 1 439 200 A1, DE 10 2007 055 485 A1 and DE 10 2008 041 601. These documents are hereby incorporated by reference and are considered to form part of the disclosure of the present invention.

In the context of the hydrosilylation, any organic unsaturated compounds can be used as reaction partners of the SiH-functional siloxanes. Preference is given to using terminally unsaturated organic compounds.

For instance, in addition to terminally unsaturated allyl-functional polyethers, other low molecular weight terminally unsaturated organic compounds may also be used.

Preference is given to using terminally unsaturated polyethers such as allyl- or methallyl-functional polyethers, particularly preferably allyl polyethers. These polyethers can be produced by known processes which can be found in the prior art. The alkoxylation of unsaturated starter compounds can be produced under base, acid, or double metal cyanide (DMC) catalysis.

As an introduction to this topic, reference is made to the monograph "*Alkylene oxides and their polymers*" by F. E. Bailey, Marcel Dekker Verlag, 1991. The production and use of DMC alkoxylation catalysts has been known since the 1960s and is outlined in U.S. Pat. Nos. 3,427,256, 3,427,334, 3,427,335, 3,278,457, 3,278,458 and 3,278,459 for example. Even more effective DMC catalysts, specifically zinc-cobalt hexacyano complexes, have been developed in the meantime, for example in U.S. Pat. Nos. 5,470,813 and 5,482,908.

The terminal hydroxyl groups of the polyethers may remain in free form or may be modified partly or completely in order to optimize compatibility in the later application matrix.

Conceivable modifications include not only further condensation or addition reactions with isocyanates for example, but also transesterifications, esterifications and etherifications. In the context of the present invention, the terminal hydroxyl groups of the polyethers preferably remain in free form or are in acetylated or methylated form.

The terminally unsaturated organic compounds that may be used are preferably alkene compounds bearing further substituents. It is possible to use, for example, allyl glycol, allyl glycidyl ether, glycerol monoallyl ether, allylanisole, allylphenol, eugenol, hexenol, C6-C20-alkene, vinylcyclohexene monoxide and also undecylenic acid or methyl undecylenoate, particular preference being given to allyl glycol, tetradecene, hexadecene, octadecene, eugenol and glycerol monoallyl ether.

In addition to or instead of terminally unsaturated compounds, it is also possible to use compounds having internal double bonds such as norbornene derivatives or even internal alkyne compounds. However, particular preference is given to using terminally unsaturated alkenes and polyethers.

In the process according to the invention, as already mentioned in the introduction, any noble metal catalyst may be used which catalyzes a SiC bond formation reaction between a SiH-functional polysiloxane and an unsaturated compound. These are well known to a person skilled in the art.

Applicable catalytically active noble metal compounds are based in particular on complexes of platinum, palladium, rhodium, ruthenium, iridium and osmium.

In the context of the present invention, preferably applicable are platinum compounds such as hexachloroplatinic acid, cis-diamminedichloridoplatinum(II) and Karstedt's catalyst. Pt(0) compounds such as the Karstedt complex are particularly preferably applicable as catalysts in accordance with the invention, particular preference being given to complexes having divinyltetramethyldisiloxane radicals.

In addition, however, other stable zerovalent platinum-olefin complexes are suitable, such as bis-(1,5-cyclooctadiene)platinum(0) and tris(norbornene)platinum(0), diplatinum tris(heptadiene-1,6), platinum ($\eta$2,$\eta$2-1,2,6,7-heptadiene-1,6) ($\eta$2-1,2-heptadiene-1,6) and platinum ($\eta$2-ethylene) ($\eta$2,$\eta$2-1,2,6,7-heptadiene-1,6).

The adsorbents that can be used are, in particular, any inorganic salts preferably having a large surface area. Suitable are acidic or basic ion exchangers, chelating agents or functionalized silica gels as well as activated carbon or carbon black.

It corresponds to a preferred embodiment of the invention when the adsorbents used are activated carbons, aluminium oxides, magnesium silicates, aluminium silicates, such as preferably zeolites or kaolinite, silica gels, functionalized silica gels, clay earths, carbon blacks, fibrous or microcrystalline celluloses, synthetic porous adsorber resins, polymer adsorbents such as crosslinked styrene polymers, molecular sieves, acidic or basic ion exchangers, and/or chelating agents, wherein aluminium silicates and/or magnesium silicates are particularly preferred.

Preferably applicable are relatively inexpensive to acquire aluminium silicates or magnesium silicates, which are advantageously provided with a high surface area.

The company The Dallas Group of America Inc. markets a broad product spectrum of magnesium silicates under the name Magnesol®, which are preferably used for purifying biodiesel.

The product spectrum offers both different molar ratios of magnesium oxide to silicon dioxide and diverse particle sizes of the adsorbents as well as different sized surface area of the solid in order to be able to offer an optimal effective profile for the respective application.

In the context of the present invention disclosure, particularly advantageously applicable are compounds having a molar ratio of $MgO:SiO_2$ from (1:5) to (1:1), preferably (1:3.6) to (1:2.7), particularly preferably (1:3.0) to (1:2.7).

The specific surface area (BET) of the solid may preferably be at least 50 to 700 m$^2$/g, particularly preferably at least 70 m$^2$/g and in a further embodiment preferably at least 350 m$^2$/g, determinable by the BET method, especially determinable in accordance with DIN ISO 9277:2014-01.

The average particle size may preferably be 10 to 100 μm, preferably 20 to 80 μm. Particularly advantageously applicable in the process according to the invention are magnesium silicates having an average particle size between 40 and 60 μm. In the context of this invention, the average particle size is the D50 value, specified as volumetric diameter. D50 signifies that 50% of the particles are smaller than the specified value. The D50 value can be determined in particular by laser diffractometry.

Another company which markets suitable adsorbents includes, for example, Kyowa Chemical Industry Co., Ltd., which offers a broad product spectrum under the name KYOWAAD®. In addition to the magnesium silicate KYOWAAD® 600, for example, also an aluminium silicate KYOWAAD® 700 and a hydrotalcite KYOWAAD® 500.

Further aluminium silicates that may be advantageously used are naturally occurring kaolin (CAS 1332-58-7), also called clay earth or china clay or particularly kaolinite (CAS 1318-74-7).

It has been found, surprisingly, that the use of adsorbents according to the invention, which are added as a further, separate component, in the context of the noble metal-catalyzed hydrosilylation of a H-functional siloxane with an unsaturated organic compound results in color-reduced, preferably colorless, final products.

The adsorbents can be added prior to and/or during the noble metal-catalyzed hydrosilylation.

In a preferred embodiment of the process according to the invention, a SiH-siloxane and an unsaturated organic compound are initially charged and temperature-adjusted, together with the adsorbents, especially comprising magnesium silicate; the noble metal catalyst is then added and the reaction mixture is stirred at the optimally adjusted temperature until the SiH value of the reaction mixture verifies a virtually quantitative conversion (>99%).

In an alternative embodiment, however, it may also be advantageous to initially charge and temperature-adjust the unsaturated organic compound with adsorbents and catalyst, and only then to add the SiH-functional siloxane in a controlled manner.

In a further preferred embodiment, it may also be advantageous to firstly initially charge the SiH-functional siloxane together with the adsorbent, then to add the catalyst and only then to add the unsaturated organic compound in a controlled manner.

After hydrosilylation is complete, the reaction mixture can be purified by distillation if required in order to remove low molecular weight impurities, for example.

Finally, the reaction mixture is freed from solid constituents, such as adsorbent for example, especially by filtration, and this gives a color-reduced, especially colorless, hydrosilylation product, particularly polyether siloxane.

It has further been found, surprisingly, that in a particularly preferred embodiment of the process, comprising the use of adsorbent and water, a qualitatively even better product may be obtained.

For instance, the visual appearance (particularly in the form of a lighter product) can be still further improved, in particular the original Pt content thereof can be even further reduced, wherein the presence of water and adsorbent has no negative influence at all on the reaction.

The amount of adsorbents used can be selected within broad ranges. Particularly with respect to cost-benefit analysis, amounts of preferably 0.05 to 5% by weight adsorbent, in a ratio to the total amount, have proven to be useful. Particular preference is given to using 0.1 to 2% by weight and particularly preferably 0.2 to 1% by weight adsorbent, % by weight based on the total reaction mass. This corresponds to a particularly preferred embodiment of the invention.

The optional amount of water used can be selected within broad ranges. Particularly with respect to cost-benefit analysis, amounts of preferably 0.05 to 50% by weight water, in a ratio to the total amount, have proven to be useful. Particular preference is given to using 0.5 to 5% by weight and especially preferably 1 to 3% by weight water, % by weight based on the total reaction mass. This corresponds to a particularly preferred embodiment of the invention.

The process according to the invention is preferably carried out under an inert atmosphere, preferably under an argon or nitrogen stream and at temperatures of preferably 50 to 130° C.

The process according to the invention may be used to produce the polysiloxane compounds described hereinbelow for example.

Preferred polysiloxane compounds obtainable according to the invention are those of the formula (I)

$$M_a M'_b M''_c D_d D'_e D''_f T_g Q_h \quad \text{formula (I)}$$

and are characterized in that
$M=[R^1_3SiO_{1/2}]$
$M'=[R^2R^1_2SiO_{1/2}]$
$M''=[R^3R^1_2SiO_{1/2}]$
$D=[R^1_2SiO_{2/2}]$
$D'=[R^2R^1SiO_{2/2}]$
$D''=[R^3R^1SiO_{2/2}]$
$T=[R^1SiO_{3/2}]$
$Q=[SiO_{4/2}]$
a=0-20, preferably 0-10, particularly preferably 2,
b=0-20, preferably 0-10, particularly preferably 0 or 2,
c=0-20, preferably 0-10, particularly preferably 0 or 2,
d=0-1000, preferably 0-500, particularly preferably 0-200,
e=0-30, preferably 1-15, particularly preferably 1-10,
f=0-30, preferably 0-15, particularly preferably 0-10,
g=0-20, preferably 0-10, particularly preferably 0-5,
h=0-20, preferably 0-15, particularly preferably 0-5, with the proviso that the sum of a+b+c+d+e+f+g+h≥3, and the sum of b+c+e+f must be ≥1, and the sum of e+f is preferably ≥1, and $R^1$=independently identical or different hydrocarbon radicals having 1-7 carbon atoms or H, preferably methyl, ethyl or phenyl, especially preferably methyl, $R^2$=independently identical or different polyether radicals, $R^3$=independently identical or different hydrocarbon radicals which have 8-20 carbon atoms and may also contain heteroatoms and may have further substitution, preferably SiC-bonded radicals resulting from alkynediol and alkoxylates thereof, allyl glycol, allyloxyethanol, allyl glycidyl ether, glycerol monoallyl ether, allylanisole, eugenol, hexenol, hexadecene, octadecene, undecylenic acid and methyl undecylenoate, particularly preferably hexadecene, octadecene, eugenol and glycerol monoallyl ether.

The preferred polysiloxane compounds of the formula (I) according to the invention are preferably obtainable by the process according to the invention described above.

The hydrosilylation products according to the invention, preferably the preferred polysiloxane compounds, especially of the formula (I), can be used for diverse applications, particularly the use as surfactants shall be mentioned. Particularly suitable is the use as dispersing additive, defoamer, wetting aid, hydrophobizing agent or crosslinking additive, preferably for use in pastes, paints, varnishes, overcoats, coatings and/or coating agents, and also in antiperspirants/deodorants, and in pharmaceutical formulations. In addition to this is the use in cleaning and/or care formulations suitable for cleaning and/or care of hard surfaces and/or suitable for cleaning, treatment and post-treatment of textiles, and also in cosmetic products. In addition to this is the further use as foam stabilizers or foam additives for polyurethane foams. In addition to this is the use as adjuvant for improving the effect of plant protection active ingredients and/or as support for plant protection active ingredients, wherein the plant protection active ingredients are preferably selected from microbiological plant protection active ingredients.

Measurement Methods:

In the context of the present invention, parameters or measurements are preferably determined using the methods described herein below. In particular, these methods were used in the examples of the present intellectual property right.

The SiH conversion of the hydrosilylation is determined by butoxide-catalyzed release of the (residual) Si—H present in the sample as elementary hydrogen and the quantitative determination thereof.

The Pt content is determined by matrix-adjusted calibration solutions on ICP-EOS (Inductively Coupled Plasma-Optical Emission Spectrometry). For this purpose, the sample to be analyzed is firstly precisely weighed and solubilized by microwave digestion with $HNO_3/HF$. Depending on the Si content—as known to a person skilled in the art-different amounts of HF are used.

Subsequently, the acid is evaporated off and the residue is taken up in aqua regia and made up to a defined volume.

The content is then determined by injecting into the ICP-OES. The sample of unknown composition is measured directly following the calibration. After the measurement, it is checked with a calibration solution that stable measurement conditions were present during the measurement. The values were determined in duplicate and the results are stated as the mean of the two measurements in ppm; up to 2 ppm, with a precision of one decimal place.

Wet chemistry analysis was performed according to international standard methods: iodine value (IV; DGF C-V 11 a (53); acid value (AV; DGF C-V 2); OH value (OHV; ASTM D 4274 C).

The Hazen color number was determined in accordance with DIN EN ISO 6271 (2005): Determination of the color of clear liquids according to the platinum-cobalt scale.

The examples which follow describe the present invention by way of example, without any intention of restricting the invention, the scope of application of which is apparent from the entirety of the description and the claims, to the embodiments specified in the examples.

In the examples detailed below, the Karstedt catalyst used was platinum (0)-1,3-divinyl-1,1,3,3-tetramethyldisiloxane, 2% dissolved in xylene.

MAGNESOL® Polysorb 3040 is a magnesium silicate from "The Dallas Group of America Inc." It was used in some examples, see examples below.

KYOWAAD® 600 is a magnesium silicate from Kyowa Chemical Industry Co., Ltd. It was used in some examples, see examples below.

Kaolinite natural (CAS: 1318-74-7) is an aluminium silicate, obtained from Sigma-Aldrich. It was used in one example; see the following examples.

EXAMPLES

Example 1a: Synthesis of an HMTS-Based Polyether Siloxane (Comparative Example)

In a 1 L flange flask provided with a dropping funnel with pressure equalization tube, thermometer, jacketed coil condenser and Sigma stirrer, 226.6 g of an allyl polyether (ethoxylate of allyl alcohol having an IV of 63 g iodine/100 g) is initially charged and the mixture heated to 90° C. with stirring and argon supply. The Karstedt catalyst is then added using a micropipette (c (batch)=4 ppm Pt). Subsequently, heptamethyltrisiloxane with a mass of 100 g (HMTS with SiH=4.50 mol/kg) is added dropwise over approx. 30 minutes via the dropping funnel such that the temperature of the reaction mixture does not exceed 115° C. After addition is complete, the mixture is further stirred at 110° C. for 1 h and then the SiH conversion is determined. This gave the SiH conversion specified in Table 1, determined by the sodium butoxide method. The mixture is then distilled for 1 h at 120° C. and p<10 mbar in order to remove volatile product constituents and then filtered through a layer filter.

Example 1b: Synthesis of an HMTS-Based Polyether Siloxane (Comparative Example)

The example was carried out analogously to Example 1a with the difference that, after addition of the allyl polyether, the amount of water also specified in Table 1 was added.

Example 1c: Synthesis of an HMTS-Based Polyether Siloxane (Inventive)

The example was carried out analogously to Example 1a with the difference that, after addition of the allyl polyether, the amount of MAGNESOL® Polysorb 3040 (based on the total mixture) specified in Table 1 was added.

Example 1d: Synthesis of an HMTS-Based Polyether Siloxane (Inventive)

The example was carried out analogously to Example 1a with the difference that, after addition of the allyl polyether, the amounts of MAGNESOL® Polysorb 3040 and water (each based on the total mixture) also specified in Table 1 were added.

Example 1e: Synthesis of an HMTS-Based Polyether Siloxane (Inventive)

The example was carried out analogously to Example 1a with the difference that, after addition of the allyl polyether, the amounts of MAGNESOL® Polysorb 3040 and water (each based on the total mixture) also specified in Table 1 were added.

Example 1f: Synthesis of an HMTS-Based Polyether Siloxane (Inventive)

The example was carried out analogously to Example 1a with the difference that, after addition of the allyl polyether, the amounts of kaolinite and water (each based on the total mixture) also specified in Table 1 were added.

TABLE 1

Additives and analytical data for Examples 1a-f

| Example | SiH conversion [%] | Adsorbent [%] | Water [%] | Hazen | Pt content [ppm] |
|---|---|---|---|---|---|
| 1a | 99.2 | 0 | 0 | 80 | 4.0 |
| 1b | 99.9 | 0 | 0.5 | 80 | 3.0 |
| 1c | 99.8 | 0.5 | 0 | 48 | 2.0 |
| 1d | 99.8 | 0.5 | 0.5 | 30 | 1.6 |
| 1e | 99.9 | 0.5 | 1.0 | 11 | 0.7 |
| 1f | 98.9 | 0.125 | 0.5 | 7 | 0.2 |

Example 2a: Synthesis of a C16-Alpha-Olefin-Based Polyalkylsiloxane (Comparative Example)

In a flange flask provided with a dropping funnel with pressure equalizing tube, thermometer and Sigma stirrer, 250 g of a comb-positioned SiH siloxane (SiH=6.88 mol/kg, $M_2D_{5.4}D^H_{6.6}$) are initially charged and the mixture is heated with stirring and argon supply to 90° C. The Karstedt catalyst (c (batch)=3 ppm Pt) is then added using a micropipette. Subsequently, the C16 alpha-olefin with a mass of 443.9 g is added dropwise over approx. 40 minutes via the dropping funnel such that the temperature of the reaction mixture does not exceed 115° C. After addition is complete, the mixture is further stirred at 110° C. for 1 h and then the SiH conversion is determined. This gave the SiH conversion specified in Table 2, determined by the sodium butoxide method.

Example 2b: Synthesis of a C16-Alpha-Olefin-Based Polyalkylsiloxane (Inventive)

The example was carried out analogously to Example 2a with the difference that, after addition of the siloxane, the amounts of MAGNESOL® Polysorb 3040 and water (each based on the total mixture) also specified in Table 2 were added.

Example 2c: Synthesis of a C16-Alpha-Olefin-Based Polyalkylsiloxane (Inventive)

The example was carried out analogously to Example 2b with the difference that the C16 alpha-olefin was initially charged and the siloxane was metered in.

TABLE 2

Additives and analytical data for Examples 2a-c

| Example | SiH conversion [%] | Adsorbent [%] | Water [%] | Hazen | Pt content [ppm] |
|---|---|---|---|---|---|
| 2a | 97.9 | 0 | 0 | 38 | 2.0 |
| 2b | 97.5 | 0.25 | 0.5 | 21 | 0.9 |
| 2c | 99.9 | 0.25 | 0.5 | 11 | 0.6 |

Example 3a: Synthesis of a Comb-Positioned Polyether Siloxane (Comparative Example)

In a 1 L flange flask provided with a dropping funnel with pressure equalization tube, thermometer, jacketed coil condenser and Sigma stirrer, 202.3 g of a methylated allyl polyether (ethoxylate of allyl alcohol having an IV of 63.5 g iodine/100 g, the terminal OH group of which was methylated) is initially charged and the mixture heated to 90° C. with stirring and argon supply. The Karstedt catalyst is then added using a micropipette (c (batch)=4 ppm Pt). Subsequently, the comb-positioned SiH siloxane with a mass of 250 g (SiH=1.50 mol/kg, $M_2D_6D^H_1$) is added dropwise over approx. 30 minutes via the dropping funnel such that the temperature of the reaction mixture does not exceed 115° C. After addition is complete, the mixture is further stirred at 110° C. for 5 h and then the SiH conversion is determined. This gave the SiH conversion specified in Table 3, determined by the sodium butoxide method. The mixture is then distilled for 2 h at 120° C. and p<10 mbar in order to remove volatile product constituents and then filtered through a layer filter.

Example 3b: Synthesis of a Comb-Positioned Polyether Siloxane (Comparative Example)

The example was carried out analogously to Example 3a with the difference that, after addition of the allyl polyether, the amount of water also specified in Table 3 was added.

Example 3c: Synthesis of a Comb-Positioned Polyether Siloxane (Inventive)

The example was carried out analogously to Example 3a with the difference that, after addition of the allyl polyether, the amount of MAGNESOL® Polysorb 3040 (based on the total mixture) also specified in Table 3 was added.

Example 3d: Synthesis of a Comb-Positioned Polyether Siloxane (Inventive)

The example was carried out analogously to Example 3a with the difference that, after addition of the allyl polyether, the amounts of MAGNESOL® Polysorb 3040 and water (each based on the total mixture) also specified in Table 3 were added.

Example 3e: Synthesis of a Comb-Positioned Polyether Siloxane (Inventive)

The example was carried out analogously to Example 3d with the difference that the absorbent KYOWAAD® 600 was added instead of MAGNESOL® Polysorb 3040.

TABLE 3

Additives and analytical data for Examples 3a-e

| Example | SiH conversion [%] | Adsorbent [%] | Water [%] | Hazen | Pt content [ppm] |
|---|---|---|---|---|---|
| 3a | >99% | 0 | 0 | 22 | 1.1 |
| 3b | >99% | 0 | 0.5 | 36 | 1.5 |
| 3c | 98.1% | 0.25 | 0 | 5 | 0.5 |
| 3d | >99% | 0.25 | 0.5 | 4 | 0.2 |
| 3e | >99% | 0.25 | 0.5 | 1 | 0.2 |

Example 4a: Synthesis of a Linear Polyether Siloxane (Comparative Example)

In a 1 L flange flask provided with a dropping funnel with pressure equalizing tube, thermometer, jacketed coil condenser and Sigma stirrer, 381.8 g of an allyl polyether (copolymer of EO (60%) and PO (40%) on allyl alcohol having an IV of 49 g iodine/100 g) and 300 g of siloxane (SiH value=1.82 mol/kg, $M_2^H D_{13}$) are successively initially charged and heated to 55° C. with stirring and under argon supply. The Karstedt catalyst is then added using a micropipette (c (batch)=6 ppm Pt). The mixture is heated to 90° C. and appropriately counter-cooled such that a temperature of 110° C. is not exceeded. Subsequently, the mixture is further stirred at 110° C. for 1 h and then the SiH conversion is determined. This gave the SiH conversion specified in Table 4, determined by the sodium butoxide method. The mixture is then distilled for 1 h at 120° C. and p<10 mbar in order to remove volatile product constituents and then filtered through a layer filter.

Example 4b: Synthesis of a Linear Polyether Siloxane (Inventive)

The example was carried out analogously to Example 4a with the difference that, after addition of the allyl polyether and siloxane, the amounts of MAGNESOL® Polysorb 3040 and water (each based on the total mixture) also specified in Table 4 were added.

TABLE 4

Additives and analytical data for Examples 4a-b

| Example | SiH conversion [%] | Adsorbent [%] | Water [%] | Hazen | Pt content [ppm] |
|---|---|---|---|---|---|
| 4a | 99.9 | 0 | 0 | 91 | 4.0 |
| 4b | 99.9 | 0.5 | 1 | 36 | 1.7 |

Conclusion

On consideration of the Hazen color numbers and Pt contents specified in Tables 1-4, it is evident to a person skilled in the art that the best products having the lowest Hazen color numbers and lowest Pt content were obtained by the process according to the invention.

Carrying out the process in the presence of adsorbents according to the invention, particularly magnesium silicate, already results in qualitatively much higher quality products. However, this quality is still further increased by using the combination of water and adsorbents, particularly magnesium silicate.

The presence of water has no negative influence at all on the hydrosilylation reaction.

The invention claimed is:

1. A process for producing organically modified polysiloxanes and/or silanes by hydrosilylation, comprising the following steps:
   a) reacting a SiH-functional siloxane and/or silane with an unsaturated organic compound in the presence of a noble metal catalyst and
   in the presence of water,
   b) distillation,
   c) final separation of solids, by filtration,
   wherein adsorbents are used in step a), which are added as a further, separate component,
   wherein the adsorbents comprise magnesium silicate.

2. The process according to claim 1, wherein the unsaturated organic compounds comprise terminally unsaturated organic compounds, and are terminally unsaturated alkene compounds, which may optionally bear further substituents, selected from the group consisting of allyl polyethers, allyl glycidyl ether, glycerol monoallyl ether, allyl glycol, allyloxyethanol, allylanisole, allylphenol, eugenol, hexenol, C6-C20-alkene, vinylcyclohexene monoxide, hexadecene, octadecene, and methyl undecylenoate.

3. The process according to claim 1, wherein the unsaturated organic compounds comprise internal double bonds or internal alkyne compounds.

4. The process according to claim 1, wherein the noble metal catalysts used are compounds or complexes of platinum, palladium, rhodium, ruthenium, iridium, and/or osmium, and of the Karstedt type.

5. The process according to claim 1, wherein the adsorbent comprises magnesium silicates, having a molar ratio of $MgO:SiO_2$ from (1:5) to (1:1).

6. The process according to claim 5, wherein the specific surface area (BET) of the magnesium silicate is at least 50 to 700 $m^2/g$ and/or, the average particle size is from 10 to 100 µm.

7. The process according to claim 1, wherein the adsorbents are used in a total amount of from 0.05% to 5% by weight, % by weight based on the total reaction mass, wherein the adsorbents are added prior to and/or during the noble metal-catalyzed hydrosilylation.

8. The process according to claim 1, wherein the hydrosilylation is carried out under an inert atmosphere, under a $N_2$ atmosphere or argon atmosphere, and/or at temperatures of from 50 to 130° C.

9. The process according to claim 1, wherein the hydrosilylation is carried out in the presence of water, which is removed by distillation after the reaction, wherein the amount of water is from 0.05% to 50% by weight, % by weight based on the total reaction mass.

10. The process according to claim 1, wherein the unsaturated organic compounds include terminally unsaturated alkene compounds, which may optionally bear further substituents including terminally unsaturated allyl polyethers.

11. The process according to claim 1, wherein the adsorbents used consist of magnesium silicates.

12. The process according to claim 1, wherein the adsorbent comprises magnesium silicates, having a molar ratio of $MgO:SiO_2$ from (1:3.6) to (1:2.7).

13. The process according to claim 5, wherein
    (a) the specific surface area (BET) of the magnesium silicate is at least from 70 to 700 $m^2/g$, and/or
    (b) the average particle size is from 20 to 80 µm.

14. The process according to claim 1, wherein the adsorbents are used in a total amount of from 0.1% to 2% by weight, % by weight based on the total reaction mass, wherein the adsorbents are added prior to and/or during the noble metal-catalyzed hydrosilylation.

15. The process according to claim 1, wherein said unsaturated organic compound is a norbornene derivative.

16. The process according to claim 1, wherein the unsaturated organic compound comprises an allyl polyether and wherein the noble catalyst comprises a Karstedt catalyst.

17. The process according to claim 1, wherein the adsorbents are added prior to the noble metal-catalyzed hydrosilylation.

18. The process according to claim 1, wherein the adsorbents are added during the noble metal-catalyzed hydrosilylation.

19. The process according to claim 1, wherein the adsorbents are added prior to and during the noble metal-catalyzed hydrosilylation.

* * * * *